United States Patent
McDonell et al.

(10) Patent No.: US 11,504,273 B2
(45) Date of Patent: Nov. 22, 2022

(54) VITRECTOMY INSTRUMENT WITH PRECISION CUTTER STOP

(71) Applicant: Alcon Inc., Fribourg (CH)

(72) Inventors: Brian William McDonell, Irvine, CA (US); Salomon Valencia, Aliso Viejo, CA (US)

(73) Assignee: Alcon Inc., Fribourg (CH)

( * ) Notice: Subject to any disclaimer, the term of this patent is extended or adjusted under 35 U.S.C. 154(b) by 687 days.

(21) Appl. No.: 16/506,500

(22) Filed: Jul. 9, 2019

(65) Prior Publication Data
US 2020/0016001 A1 Jan. 16, 2020

Related U.S. Application Data

(60) Provisional application No. 62/697,463, filed on Jul. 13, 2018.

(51) Int. Cl.
*A61F 9/007* (2006.01)
*A61B 17/32* (2006.01)
*A61B 17/3207* (2006.01)

(52) U.S. Cl.
CPC .... *A61F 9/00763* (2013.01); *A61B 17/32002* (2013.01); *A61B 17/320783* (2013.01); *A61B 2017/320028* (2013.01)

(58) Field of Classification Search
CPC .......... A61F 9/00763; A61B 17/32002; A61B 17/320783; A61B 2017/320028; A61B 2017/00539; A61B 2017/00544
See application file for complete search history.

(56) References Cited

U.S. PATENT DOCUMENTS

| | | | |
|---|---|---|---|
| 5,176,628 A | 1/1993 | Charles | |
| 8,038,692 B2 | 10/2011 | Valencia | |
| 8,187,293 B2 | 5/2012 | Kirchhevel | |
| 8,579,929 B2 | 11/2013 | Mackool | |
| 8,888,802 B2 | 11/2014 | Underwood | |
| 9,060,841 B2 | 6/2015 | Mccawley | |
| 9,101,442 B2 | 8/2015 | Mcdonell | |
| 9,517,161 B2 | 12/2016 | Underwood | |
| 9,693,898 B2 | 7/2017 | Farley | |
| 10,369,046 B2 | 8/2019 | Mcdonell | |
| 10,639,197 B2 | 5/2020 | Lopez | |
| 2007/0129732 A1 | 6/2007 | Zacharias | |
| 2008/0172077 A1 | 7/2008 | Valencia | |
| 2012/0158006 A1* | 6/2012 | McDonell | A61F 9/00763 606/107 |
| 2014/0171997 A1 | 6/2014 | Nissan | |
| 2014/0364886 A1 | 12/2014 | Underwood | |
| 2015/0173948 A1 | 6/2015 | Heeren | |
| 2018/0104101 A1 | 4/2018 | Lopez | |

* cited by examiner

*Primary Examiner* — Tan-Uyen T Ho
*Assistant Examiner* — Rachel S Highland

(57) ABSTRACT

Provided herein are vitrectomy instruments and related systems and methods in which the vitrectomy instruments may include a forward needle stop and a cutter stop to reduce dimensional variation of a cutter of the vitrectomy instruments, allowing for a location of the port formed in a needle of the cutter to be positioned closer to a distal tip of the cutter. With the port located closer to a distal end of the cutter, the port is able to be positioned closer to the retina of an eye.

24 Claims, 4 Drawing Sheets

VITRECTOMY INSTRUMENT WITH PRECISION CUTTER STOP

PRIORITY CLAIM

This application claims the benefit of priority of U.S. Provisional Patent Application No. 62/697,463, titled "VITRECTOMY INSTRUMENT WITH PRECISION CUTTER STOP" filed Jul. 13, 2018, whose inventors are Brian William McDonell and Salomon Valencia, which is hereby incorporated by reference in its entirety as though fully and completely set forth herein.

TECHNICAL FIELD

The present disclosure is directed to systems, instruments, and methods for use in medical procedures, and, more particularly, to systems, instruments, and methods for vitrectomy and related procedures.

BACKGROUND

Vitreoretinal procedures are commonly performed within the posterior segment of the human eye to treat many serious conditions of the posterior segment of the eye. In particular, vitreoretinal procedures may treat conditions such as age-related macular degeneration (AMD), diabetic retinopathy and diabetic vitreous hemorrhage, macular hole, retinal detachment, epiretinal membrane, cytomegalovirus (CMV) retinitis, and many other ophthalmic conditions.

Such procedures frequently involve the cutting and removal of portions of the vitreous humor from the posterior segment of the eye. The vitreous humor is formed of microscopic fibers or strands within the posterior segment. A surgeon may perform vitreoretinal procedures with a microscope and special lenses designed to provide a clear image of the posterior segment. Several tiny incisions just a millimeter or so in size are typically made on the sclera at the pars plana. In a vitrectomy procedure, the surgeon inserts microsurgical instruments through the incisions, including a vitrectomy probe or tip to cut and remove the strands of the vitreous body.

Examples of vitrectomy instruments are disclosed, for example, in U.S. Pat. Nos. 5,176,628, 8,038,692, U.S. Patent Application No. 2008/0172077, U.S. Patent Application No. 2014/0171997, U.S. Patent Application No. 2014/0364886, and U.S. Patent Application No. 2015/0173948. Mechanisms for driving a reciprocating cutter of a vitrectomy instrument and other common features and functions of vitrectomy instruments are known, for example from U.S. Pat. No. 8,038,692 and the ULTRAVIT® vitrectomy instrument produced by Alcon Laboratories, Inc., located at 6201 South Freeway, Fort Worth, Tex. 76134, and therefore the details of such mechanisms are not repeated herein.

The removal of vitreous fibers is a sensitive procedure that should be performed efficiently and without damage to the retina or other parts of the eye.

SUMMARY

The present disclosure provides for improvements in vitrectomy instruments and associated systems and methods.

An aspect of the present disclosure encompasses a vitrectomy instrument that may include a housing, a reciprocating cutter, and a motor. The housing may include a proximal end and a distal end. The reciprocating cutter may include a needle projecting from the distal end of the housing. The needle may include a proximal end, a distal end, a first lumen, and a port disposed at the distal end of the needle. The port may provide fluid communication between the exterior of the needle and the first lumen. The reciprocating cutter may also include an inner tube that extends within the first lumen of the needle. The inner tube may include a second lumen and a cutting edge adapted to cut tissue drawn into the port. The reciprocating cutter may also include a needle stop coupled to the proximal end of the needle and comprising a first contact surface and a cutter stop coupled to the inner tube and. The first contact surface may be configured to contact the second contact surface limiting distal movement of the inner tube and defining a fully extended position of the inner tube. The motor may be operable to reciprocate the inner tube.

A second aspect, the disclosure describes a method of assembling a vitrectomy instrument. The method may include forming a first assembly that may include coupling an inner tube of a cutter to a diaphragm and coupling a needle stop proximal component of a needle stop to the housing; forming a second assembly that may include assembling a needle of the cutter and needle stop distal component of the needle stop together; positioning the inner tube at a desired position within the first assembly; combining the second assembly to the first assembly that may include positioning the needle stop distal component over the needle stop proximal component; and affixing the second assembly to the first assembly that may include fixing the needle stop distal component to the needle stop proximal component.

The various aspects may include one or more of the following features. The motor may include a diaphragm disposed in the housing and movable in response to pneumatic pressure. The diaphragm may be connected to the inner tube of the reciprocating cutter such that the inner tube is movable with the diaphragm. The diaphragm may include a rigid diaphragm part connected to the inner tube and a flexible membrane connected to the rigid diaphragm part and to the housing. The cutter stop and the needle stop may be formed from a metal. The cutter stop and the inner tube may be formed from a metal, and the cutter stop may be welded to the inner tube. The cutter stop may include a stop ring that is welded to the inner tube. The cutter stop may include a stop ring. The cutter stop may also include a stop pad, and the second contact surface may be a surface of the stop pad. The needle stop may also include a needle stop proximal component and a needle stop distal component coupled to the needle stop proximal component. The needle stop proximal component may be received into a cavity defined by the needle stop distal component. The needle stop proximal component may include a proximal portion having a first cross-sectional size, a distal portion having a second cross-sectional size smaller than the first cross-sectional size, and a shoulder joining the proximal portion and the distal portion. The proximal portion of the needle stop proximal component may be received into a cavity defined by the needle stop distal component. The needle stop proximal component may be welded to the needle stop distal component. The shoulder may define the first contact surface.

The various aspects may also include one or more of the following features. Combining the second assembly to the first assembly may also include adjusting a position of the second assembly relative to the first assembly until a desired position of the second assembly is reached. Affixing the second assembly to the first assembly may include fixing the needle stop distal component to the needle stop proximal component. Fixing the needle stop distal component to the needle stop proximal component may include welding the needle stop distal component to the needle stop proximal component.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the accompanying drawings and the following detailed description.

BRIEF DESCRIPTION OF THE DRAWINGS

The accompanying drawings illustrate implementations of the devices and methods disclosed herein and, together with the description, serve to explain the principles of the present disclosure.

Figure 1:
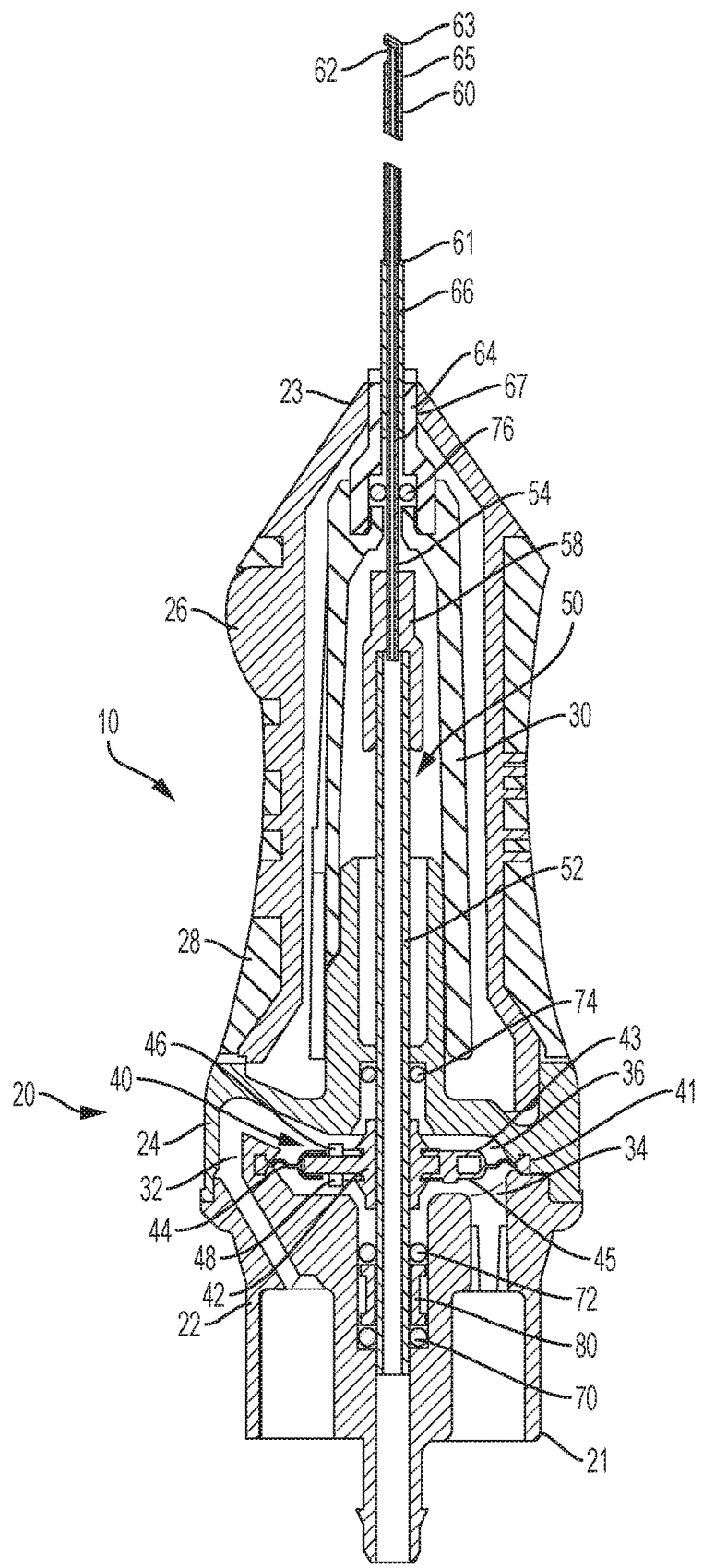
FIG. 1 is a cross-sectional view of a vitrectomy instrument having a cutter end stop on a diaphragm.

The accompanying drawings may be better understood by reference to the following detailed description.

DETAILED DESCRIPTION

For the purposes of promoting an understanding of the principles of the present disclosure, reference will now be made to the implementations illustrated in the drawings, and specific language will be used to describe the same. It nevertheless will be understood that no limitation of the scope of the disclosure is intended. Any alterations and further modifications to the described devices, instruments, or methods, and any further application of the principles of the present disclosure, are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure. For simplicity, in some instances the same reference numbers are used throughout the drawings to refer to the same or like parts.

FIG. 1 is an example of a vitrectomy instrument 10 similar to the ULTRAVIT® vitrectomy instrument. The vitrectomy instrument 10 includes cutter stops 46 and 48 on a diaphragm 40. The vitrectomy instrument 10 includes a housing 20 having a proximal end 21 and a distal end 23. The housing 20 includes a proximal motor housing 22, a distal motor housing 24, a first forward housing part 26, and a second forward housing part 28. The first and second forward housing parts 26, 28 may be made of different materials. For example, the first forward housing part 26 may be made of a rigid material, and the second forward housing part 28 may be made of a soft material to facilitate gripping. The vitrectomy instrument 10 also includes a retainer 30 that, in addition to the housing 20, serves to help position and guide the needle 60 and reciprocating cutter 50.

As indicated above, the vitrectomy instrument 10 includes a diaphragm 40 disposed in a diaphragm chamber 36. The diaphragm 40 is attached to the housing 20 around a perimeter 41 of the diaphragm 40. The diaphragm 40 is movable within the diaphragm chamber 36 in response to pneumatic pressure. A first pneumatic passage 32 is in fluid communication with the diaphragm chamber 36 and is operable to communicate pneumatic pressure to a distal side 43 of the diaphragm 40. A second pneumatic passage 34 is also in fluid communication with the diaphragm chamber 36 and is operable to communicate pneumatic pressure to a proximal side 45 of the diaphragm 40. Alternating application of differential pneumatic pressures to the first pneumatic passage 34 and the second pneumatic passage 36 causes the diaphragm 40 to oscillate within the diaphragm chamber 36.

The diaphragm 40 is coupled to an inner tube 54 of a cutter 50. The cutter 50 includes the inner tube 54, a needle 60 that projects distally from the distal end 23 of the housing 20, and a driveshaft 52 coupled to the inner tube 54 via a coupling 58. Oscillation of the diaphragm 40 is transferred to the inner tube 54 via the drive shaft 52, causing the inner tube 54 to oscillate within the needle 60. The needle 60 includes a proximal end 61, a distal end 63, and a port 62 formed in a sidewall 65 of the needle 60 at the distal end 63 thereof. The needle 60 is connected to a stiffener sleeve 66. In some instances, the needle 60 may extend through a lumen formed within the stiffener sleeve 66. In other implementations, the needle 60 may attach to a distal end of the stiffener sleeve 66. The needle 60 and stiffener sleeve 66 are attached to a needle holder 64 located the distal end 23 of the housing 20. As shown in FIG. 1, the needle holder 64 is received into an opening 67 formed at the distal end 23 of the housing 20. The needle holder 64 is bonded to the retainer 30.

The diaphragm 40 includes a rigid diaphragm part 42 and a flexible membrane 44. The rigid diaphragm part 42 is located in a central portion of the diaphragm 40 and couples to the inner tube 54 of the cutter 50 via the drive shaft 52. The diaphragm 40 is operable to oscillate thereby producing a reciprocating action of the inner tube 54.

The diaphragm 40 also includes a first cutter stop 46 and a second cutter stop 48. The first cutter stop 46 is operable to contact a portion of the housing 20 when the diaphragm 40 is fully displaced distally within the diaphragm chamber 36. Thus, the first cutter stop 46 contacts the housing 20 to limit an amount of distal movement of diaphragm 40 and the inner tube 52 of the cutter 50. Similarly, the second cutter stop 48 is operable to contact a portion of the housing 20 when the diaphragm 40 is fully displaced proximally within the diaphragm chamber 36. Accordingly, the second cutter stop 48 contacts the housing 20 to limit an amount of proximal movement of the diaphragm 40 and the inner tube 52 of the cutter 50.

Figure 2:
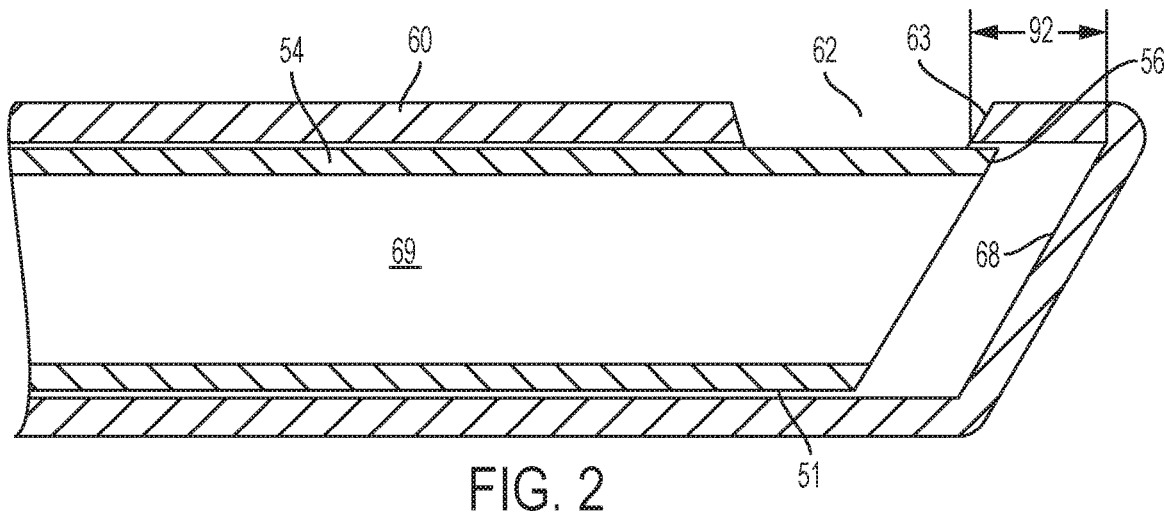
FIG. 2 is a cross-sectional view of a distal end of an example vitrectomy instrument.

As mentioned above, the inner tube 54 extends within the needle 60. As shown in FIG. 2, the inner tube 54 has a cutting edge 56 formed at a distal end 51 of the inner tube 54. The cutting edge 56 of the inner tube 54 cooperates with the port 62 and, particularly with an edge 63 of the port 62, to sever materials, such as tissue, drawn into the port 62. The needle 60 includes a beveled, closed distal end 68.

The vitrectomy instrument 10 also includes elastomeric O-rings 70, 72, 74, and 76 that sever as seals to isolate fluidically various areas within the vitrectomy instrument 10. A spacer 80 is located between O-rings 70 and 72 and functions to keep O-rings 70 and 72 separated and located in desired respective positions. A vent (not shown) may be provided in the housing 20 adjacent the spacer 80 to allow venting of excess pressure.

During use of the vitrectomy instrument 10, the needle 60 may be inserted into the eye of a patient with the port 62 positioned adjacent tissue to be removed. For example, the needle 60 may be positioned adjacent to vitreous fibers for the removal thereof. With suction applied to a lumen 69 formed in the inner tube 54, the inner tube 54 is caused to reciprocate at high speed within the needle 60 with the cutting edge 56 moving back and forth across the port 62. In some implementations, the reciprocating motion of the inner tube 54 may be caused by pneumatic actuation. As shown in FIG. 1, for example, pneumatic pressure may be alternatingly applied to the diaphragm 40 via the pneumatic passages 32, 34, causing the diaphragm 40 to move back and forth at high speed. Because the diaphragm 40 is connected to the inner tube 54, the back and forth movement of the diaphragm 40 causes reciprocating motion of the inner tube 54. The suction applied to the lumen 69 acts through the port 62 to draw vitreous fibers into the port 62. As the inner tube 54 moves distally across the port 62, the cutting edge 56 acts in conjunction with the edge 63 of the needle 60 to sever the vitreous fibers. The suction applied to the lumen 69 removes the severed vitreous fibers.

The forward and backward movement of the inner tube 54 is stopped by contact between the housing 20 and the first and second cutter stops 46, 48. In a vitrectomy instrument, such as the vitrectomy instrument 10 shown in FIG. 1, a location of the cutting edge 56 of the inner tube 54 relative to the distal end 68 of the needle 60 when the first cutter stop 46 contacts the housing 20 can lack precision. This lack of precision may be the result of the number of components involved in transmitting motion from the diaphragm 40 to the cutter and components associated securing parts of the cutter within the vitrectomy instrument 10; the materials forming those components; and the manner in which many of those components are joined. For example, the driveshaft 52, coupling 58, and needle holder 64 may be formed of plastic, and the dimensions of these parts may change due to temperatures changes over time due, for example, to internal stresses. In addition, many of these parts may be joined with an adhesive. For example, the stiffener sleeve 66 and the needle holder 64 may be joined by an adhesive; the needle holder 64 and the forward housing part 26 may be joined by an adhesive; the connections between the coupling 58 and the driveshaft 52 and between the coupling 58 and the inner tube 54 may also be made with an adhesive; the driveshaft 52 and the rigid diaphragm part 42 may be joined with an adhesive; the needle holder 64 may be adhesively bonded to the retainer 30; and the retainer 30 may be adhesively bonded to the housing 20. Adhesive joints may also change over time due, for example, to changes in temperature. These changes cause the dimensions between the parts to vary from a target dimension and particularly from an established dimension obtained during manufacturing.

Once the vitrectomy instruments are manufactured, the vitrectomy instruments may be subjected to thermal cycling (i.e., one or more cycles of changes in temperature) during shipping and storage prior to use. This thermal cycling can cause dimensional distortions to the components, resulting in altered dimensions, where even small dimensional changes may have a significant impact with regard to ophthalmic surgical procedures. Similarly, adhesive connections may also be detrimentally affected by thermal cycling. Thermal cycling may cause dimensional changes to adhesive connections that can adversely affect ophthalmic surgical instruments, including vitrectomy instruments.

Vitrectomy instruments, such as the vitrectomy instrument 10 shown in FIG. 1, may be designed to take these dimensional changes to ensure safe operation of the vitrectomy instrument. As a result, dimensions and tolerances of the vitrectomy instruments may be made larger than would otherwise be required if these dimensional changes did not occur. As a result, a distance 92, described in more detail below, may be made larger in order to account for the possible dimensional changes. With an increased distance 92, the port 62 may be located farther from a tissue or membrane within the eye. Use of metal parts and metal parts that are welded together dramatically reduce or avoid these problems.

In addition, the vitrectomy instrument 10 may have a number of molded plastic components, such as the needle holder 64, the retainer 30, the housing 20, the diaphragm 40, and the coupling 58. The potential for positional variations during manufacturing and different thermal expansion characteristics, particularly as compared to the metallic needle 60 and cutter tube 54, introduces further possibility of dimensional variations, also leading to imprecision in the location of the forward stroke of the cutting edge 56 relative to the port 62.

At each of these connections, slight variations may occur, as explained above. Because of the precise nature of vitrectomy instruments, these dimensional changes, although small, may combine to cause small changes in distances within the vitrectomy instruments. However, these small changes, when considered in light of the small dimensions related to some of the parts of the vitrectomy instrument, particular with respect to the cutter, may be significant. As a result, these dimensional changes may prevent the vitrectomy instruments from being as efficacious as would otherwise be possible if the number of components were reduce, the use of plastic components were reduced or eliminated, and use of adhesive connections were reduced and/or eliminated. For example, these dimensional changes may cause a position of the distal end 68 of the needle 160 relative to the housing 20 to vary or a location of the cutting edge 56 in the fully extended condition (i.e., when the first cutter stop 46 contacts the housing 20) relative to the distal end 68 of the needle to vary. As a result, the port 62 may have to be located farther from the distal end 68 of the needle 60 than would otherwise be necessary in order to accommodate changes to the vitrectomy instrument 100 that may occur, as described above. With the port 62 located farther from the distal end 68, the vitrectomy probe 10 may be less efficacious in removing vitreous fibers, especially those located close to or connected to the retina.

Because of this, the vitrectomy instruments may have had to be designed to accommodate these dimensional changes, resulting in vitrectomy instruments that are less efficacious. For example, in order to ensure that the cutting edge 56 of the inner tube 54 would be able both to cross fully the port 62 of the needle 60 and not to hit the distal end 68 of the needle 60, the needle port 62 is located a distance 92 away from the end 68 of the needle 60, as shown in FIG. 2. With the port 62 located at this position, a user, such a surgeon, may have difficulty removing vitreous fibers in some locations within an eye.

Figure 3:
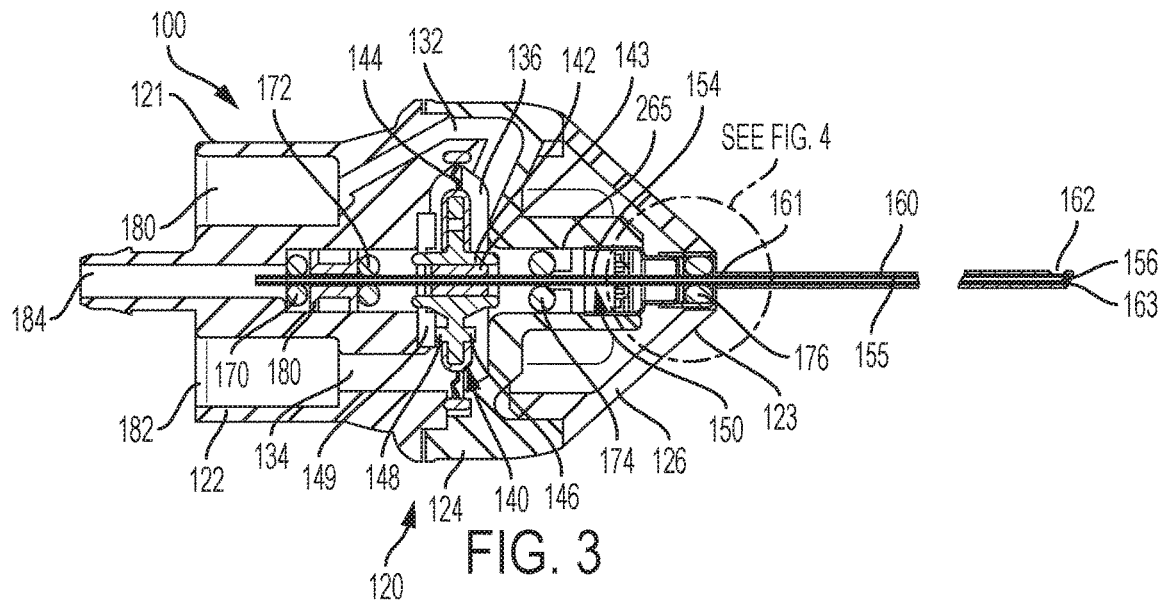
FIG. 3 is a cross-sectional view of another example vitrectomy instrument in accordance with the present disclosure.

FIG. 3 is a cross-sectional view of an example vitrectomy instrument 100 in accordance with the present disclosure. The vitrectomy instrument 100 includes a housing 120 having a proximal end 121, a distal end 123, a proximal motor housing 122, a distal motor housing 124, and a distal end housing 126.

The vitrectomy instrument 100 also includes a motor operable to reciprocate an inner tube 154 of a reciprocating cutter 150. In the illustrated example, the motor is in the form of a diaphragm 140. However, the scope of the disclosure is not so limited. In other instances, the motor may be an electric motor, a hydraulically actuated device, or some other component or group of components operable to reciprocate the inner cutter 154. The diaphragm 140 includes a rigid diaphragm part 142 and a flexible membrane 144. The diaphragm 140 is located within a diaphragm chamber 136 and divides the diaphragm chamber 136 into a proximal portion and a distal portion. A first pneumatic passage 132 is in fluid communication with a distal portion of the diaphragm chamber 136, and a second pneumatic passage 134 is in fluid communication with a proximal portion of the diaphragm chamber 136. The diaphragm 140 also includes a first cutter stop 146 and a second cutter stop 148. At the proximal portion of the diaphragm chamber 136, the vitrectomy instrument 100 includes a damper 149 that provides a contact surface operable to contact the second cutter stop 148 when the diaphragm 40 is fully displaced in the proximal direction.

Although the first cutter stop 146 is shown in FIG. 2 as being a distally-extending protrusion, and the second cutter stop 148 is shown in FIG. 2 as being a extending-proximally protrusion, the vitrectomy instrument 100 may include a plurality of each of the first and second cutter stops 146 and 148. Further, as also shown, the first cutter stop 146 and the second cutter stop 148 form part of a unitary component, i.e., the rigid diaphragm part 142. In some instances, the rigid diaphragm part 142 may be in the form of a ring, and each of the first cutter stop 146 and the second cutter stop 148 may form one or more protrusions that extend from the ring. The protrusions forming the first cutter stop 146 and the second cutter stop 148 may be arranged symmetrically or unsymmetrically around the rigid diaphragm part 142. The damper 149 may also be in the form of a ring that is adapted to contact the one or more protrusions forming the cutter stop 148. Additionally, as shown, the damper 149 is disposed at a proximal end of the diaphragm chamber 136, and, in the illustrated implementation, the damper 149 is received into a recess formed in the proximal motor housing 122. In other implementations, the damper 149 may be arranged in the diaphragm chamber 136 in other ways.

In some implementations, the first cutter stop 146 may be omitted. For example, the first cutter stop 146 may be omitted because a needle stop 260 (described in more detail below) and a third cutter stop 250 (discussed in more detail below) may exclusively be used to limit a stroke of the inner cutter 254 in the distal direction. Thus, in some implementations, inclusion of the first cutter stop 146 may be redundant. However, redundancy may be desirable out of safety in order to ensure desired operation of the vitrectomy instrument 100.

The diaphragm 140 also includes a spacer 143 disposed annularly between the inner cutter 154 and the rigid diaphragm part 142. The spacer 143 connects the inner tube 154 to the diaphragm 140. In some instances, the spacer 143 may be considered to form part of the rigid diaphragm part 142 and may be formed of the same or a similar material as the rigid diaphragm part 142.

In other implementations, the spacer 143 may be formed of a compliant material, such as, for example, an elastomeric material. Further, in some implementations, the third cutter stop 250 and the first cutter stop 146 may be configured to contact the needle stop 260 and the distal motor housing 124, respectively, at different points along the distal travel of the inner tube 154. For example, with the spacer 143 formed of a compliant material, when the third cutter stop 250 contacts the needle stop 260 and the first cutter stop 146 not having contacted the distal motor housing 124, the compliant spacer 143 may permit the diaphragm 140 (e.g., the rigid diaphragm part 142) to continue to move distally due to the compliance of the spacer 143. With continued motion of the diaphragm 140 (e.g., the rigid diaphragm part 142) in the distal direction, the first cutter stop 146 may be used to stop motion of the diaphragm 140 even after the third cutter stop 250 and the needle stop 256 have engaged to stop distal movement of the inner tube 154. In such instances, the spacer 143 may operate to slow (and in some cases even stop distal motion of the diaphragm 140 before engagement of the first cutter stop 146 with the distal motor housing 124) due to the compliance of the spacer 143. Thus, the spacer 143 formed of a compliant material may reduce vibration and noise of the vitrectomy instrument 100 during operation by increasing a time over which the diaphragm 140 comes to a stop and/or absorbing some of the kinetic energy of the diaphragm 140 before the first cutter stop 146 contacts the distal motor housing 124.

The vitrectomy instrument 100 includes a needle 160 projecting from the distal end 123 of the housing 120. The needle 160 has a proximal end 161, a distal end 163, and a port 162 formed in the needle 160 at the distal end 163. The distal end 163 of the needle 160 is closed. The port 162 provides fluid communication between an interior lumen of the needle 160 and an exterior or the needle 160. In some implementations, the needle 160 may include more than one port 162 at the distal end 163 of the needle 160.

The vitrectomy instrument 100 also includes a reciprocating cutter 150. The reciprocating cutter 150 includes the inner tube 154 that extends inside of the needle 160. In some implementations, the needle 160 and the inner cutter 154 are formed from a metal. The inner tube 154 defines a lumen 155 and is adapted to reciprocate back and forth within the needle 160. The inner tube 154 has a cutting edge 156 formed at a distal end thereof and adapted to cut tissue drawn into the port 162. In some implementations, the inner tube 154 may have an aperture that aligns with the needle port 162 when the inner tube 154 is a distal most or fully extended position. In the vitrectomy instrument 100 of FIG. 3, the reciprocating cutter 150 excludes a drive shaft and coupling, such as the drive shaft 52 and coupling 58 of the vitrectomy instrument 10 shown in FIG. 1. However, in other implementations, the vitrectomy instrument 100 may include a driveshaft and a coupling. As explained above, the diaphragm 140 connects to the inner tube 154 via the spacer 143.

The vitrectomy instrument 100 also includes several elastomeric O-rings 170, 172, 174, 176 that serve as seals to fluidically isolate various areas within the vitrectomy instrument 100. A spacer 180 is located between O-rings 170 and 172 and functions to keep O-rings 170 and 172 in position. A vent (not shown) may be provided in the housing 120 adjacent the spacer 180 to allow venting of excess pressure. A vent (not shown) may also be provided in the needle stop proximal component 264 (described in more detail below) and/or in the distal end housing 126 to allow venting of excess pressure. The O-ring 176 provides a seal operable to seal a space between the inner tube 154 and the needle 160

Figure 4:
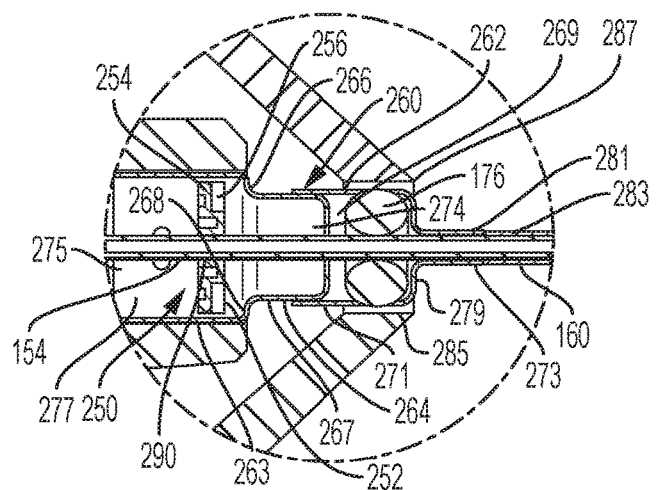
FIG. 4 is an enlarged view of a portion of the example vitrectomy instrument of FIG. 3.

As shown more clearly in the enlarged view of FIG. 4, the vitrectomy instrument 100 includes the third cutter stop 250.

The third cutter stop 250 includes a cutter stop surface 252. The third cutter stop 250 is connected to the inner tube 154. In some instances, the third cutter stop 250 may be directly connected to the inner tube 154. In other instances, the third cutter stop 250 may be indirectly coupled to the inner tube 154.

The third cutter stop 250 includes a stop ring 254 and a stop pad 256. In some instances, the stop ring 254 and the cutter tube 154 may be formed from a metal. For example, both the stop ring 254 and the cutter tube 154 may be formed from stainless steel. In some implementations, the stop ring 254 may be joined to the cutter tube 154 by a welded connection. The stop pad 256 may be formed from a metal or from a different material. For example, in other implementations, the stop pad 256 may be formed from a plastic or an elastomer, in order to avoid metal-on-metal contact when the third cutter stop 250 contacts the needle stop 260, as described below. While stop pad 256 may be formed from a plastic or elastomer, the size of the stop pad 256 may generally be small, even in the context to the other components of the vitrectomy instrument 100 that are small in nature in order to access the interior of an eye. Therefore, changes in dimensions of the stop pad 256 are also small and any effect on operation of the vitrectomy instrument 100 is likely negligible.

As also shown more clearly in the enlarged view of FIG. 4, the vitrectomy instrument 100 of FIG. 3 also includes a needle stop 260. The needle stop 260 includes a needle stop distal component 262 and a needle stop proximal component 264. The needle stop proximal component 264 includes a proximal portion 263 and a distal portion 267. The proximal portion 263 of the needle stop proximal component 264 is received into a bore 265 formed by the distal motor housing 124. In some instances, the needle stop proximal component 264 is cylindrical and has a circular cross-sectional shape. However, in other implementations, the cross-sectional shape of the needle stop proximal component 264 may be noncircular.

The needle stop proximal component forms a cavity 275. The cavity 275 has a first portion 277 defined by the proximal portion 263 and a second portion 274 defined by the distal portion 267. The distal portion 267 has a reduced cross-sectional size such that the first portion 277 of the cavity 275 is larger is cross-sectional size than the second portion 274 of the cavity 275. The inner tube 154 extends through the cavity 275 with the third cutter stop 250, coupled to the inner tube 154, disposed in the first portion 277 of the cavity 275. A shoulder 266 defining a needle stop surface 268 extends between the proximal portion 263 and the distal portion 267. The needle stop surface 268 acts to limit the forward motion of the inner tube 154 when the cutter stop surface 252 of the third cutter stop 250 contacts the needle stop surface 268, thereby stopping forward motion of the inner tube 154. During operation of the vitrectomy instrument 100, the third cutter stop 250 is prevented from moving distally beyond the first portion 277 of the cavity 275 and, hence, beyond the proximal portion 263 of the needle stop proximal component 264 because of contact between the third cutter stop 250 and the shoulder 266 of the needle stop proximal component 264.

In the example shown, the needle stop distal component 262 has a slightly enlarged cross-sectional size as compared to the cross-sectional size of the distal portion 267 of the needle stop proximal component 264. The needle stop distal component 262 forms a cavity 269 that receives the distal portion 267 of the needle stop proximal component 264 such that an exterior surface of the distal portion 267 contacts an inner surface of the needle stop distal component 262. The needle stop proximal component 264 and the needle stop distal component 262 may be joined via a welded connection at the interface between the distal portion 267 of the needle stop proximal component 264 and the needle stop distal component 262.

The needle stop distal component 262 includes a proximal portion 271 and a narrowed distal portion 273 joined by a shoulder 279. The distal end 273 abuts a proximal end 283 of the needle 260. The needle 260 may be butt welded to the distal portion 281 of the needle stop distal component 262. The proximal portion 271 of the needle stop distal component 262 is received into an opening 285 formed at the distal end 123 of the housing 120. In the illustrated example, the shoulder 279 aligns with a distal end 287 of the opening 285.

As shown in FIG. 4, the O-ring 176 is captured within the needle stop distal component 262. The needle stop 260, including both the needle stop distal component 262 and the needle stop proximal component 264, and the needle 160 may be formed from a metal. For example, the needle stop distal component 262, the needle stop proximal component 264, and the needle 160 may be formed from stainless steel. As explained above, the needle stop distal component 262 may be joined to the needle 160 by a welded connection. Similarly, the needle stop proximal component 264 and the needle stop distal component 262 may be joined together by a welded connection. In alternative embodiments, the needle stop 260 may be formed from more than two components.

During use, the needle 160 may be inserted into an eye of a patient with the port 162 disposed adjacent to tissue for which removal is desired, e.g., vitreous fibers. Suction pressure (i.e., a vacuum) may be applied to the port 262 via the lumen 155 of the cutter tube 154. The cutter tube 154 may be reciprocated at high speed by alternatingly applying pneumatic pressure to opposing sides of the diaphragm 140 via pneumatic passages 132 and 134. As a result, the cutting edge 156 of the inner tube 154 moves back and forth across the port 162. The suction applied to the port 162 draws vitreous fibers into the port 162. As the inner tube 154 moves distally across the port 162, the cutting edge 156 severs the vitreous fibers, and the severed fibers are suctioned away and removed. In some implementations, the inner tube 154 may include an aperture that aligns with the needle port 162 when the inner tube 154 is in the fully extended position, thereby allowing tissue to be drawn into the port 162 when the inner tube 154 is in the fully extended position.

Figure 5:
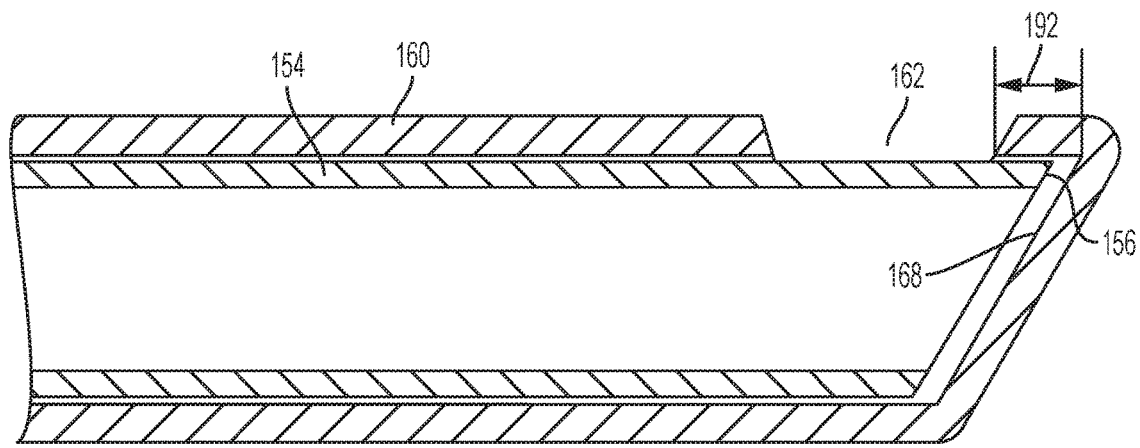
FIG. 5 is a cross-sectional view of a distal end of the example vitrectomy instrument of FIG. 3.

The forward movement of the inner tube 154 is stopped by the third cutter stop 250 contacting the needle stop 260. In particular, the cutter stop surface 252 contacts the needle stop surface 268, thereby stopping the forward motion of the inner tube 154 at that location. When contact between the cutter stop surface 252 contacts the needle stop surface 268, the cutting edge 156 of the inner tube 154 has fully traversed the port 162 in the distal direction but has not contacted the distal end 168 of the needle 160, as shown in FIG. 5.

As a result of the interaction between the third cutter stop 250 and the needle stop 260, a position of the cutting edge 265 relative to the distal end 168 of the needle is more precisely controlled when the inner tube 154 is at the fully extended position. This is due, for example, to the distal location of the third cutter stop 250, reducing the number and type of parts, and a reduction in adhesive connections within the vitrectomy instrument 100. Additionally, the design of the vitrectomy instrument 100 avoids or significantly reduces the existence of molded components, adhesive joints, and/or mismatched materials therewithin.

For example, forming welded connections between the needle 160 and the needle stop distal component 262, and between the needle stop distal component 262 and the needle stop proximal component 264 reduces dimensional variation that may occur with the use of polymeric parts and/or adhesive joints. Additionally, the stop ring 254 is welded to the cutter tube 154. Consequently, the dimensions of the cutter 150 remains unchanged or substantially unchanged in contrast to a cutter that includes polymeric components and adhesive joints. Dimensions may be considered remain substantially unchanged where the changes may, for example, occur due to thermal expansion or contraction or flexing of the vitrectomy instrument in response to pressurizing of the vitrectomy instrument (e.g., introduction of pneumatic pressure used to operate the vitrectomy instrument).

Thus, with the use of fewer components and improved dimensional accuracy associated with metal parts welded to other metal parts, the vitrectomy instrument 100 enjoys reduced dimensional variation, which allows for better positional control of the inner tube 154 at the fully extended position and position of the port 162 located closer to the distal end 160 of the needle 160.

The welded connections reduce dimensional variation as compared to molded parts and adhesive joints, leading to increased precision of the cutting edge 156 relative to the port 162 when the inner tube 154 is in the fully extended position. In addition, few components are used. Additionally, by using components formed of similar materials, e.g., in instances where the parts are formed from the same or similar metals, the thermal expansion properties of the components are similar. The thermal matching and similarity of components further reduces dimensional variation, also leading to increased precision of the cutting edge 156 relative to the port 162 when the inner tube 154 is in the fully extended position.

As a result, the vitrectomy instrument 100 has less dimensional variability, providing for improved dimensional precision, including improved positional accuracy of the inner tube 154 during actuation. As shown in FIG. 5, the port 162 is located a shorter distance 192 from the distal end 168 of the needle 160, while still providing the cutting edge 156 of the cutter tube 154 the ability to fully cross the port 162 of the needle 160 and avoid contacting the end 168 of the needle 160. This results in the ability of the port 162 to be placed more closely to structures within the eye. For example, having the port 162 closer to the distal end of the needle 160 facilitates removal of vitreous fibers located closer to the retina and/or facilitates membrane dissection and removal. Having the port 162 closer to the distal end of the needle 160 can also facilitate positioning the port 162 between a membrane and the retinal surface prior to dissection. With a shorter distance 192, a portion of the needle 160 from the distal end 168 up to a distal end of the port 162 may be inserted in between a membrane and the retina of an eye in order to manipulate the membrane (e.g., using the needle 160 as a "pick") or to gain access to the membrane in order to remove the membrane via operation of the cutter 150.

Figure 6:
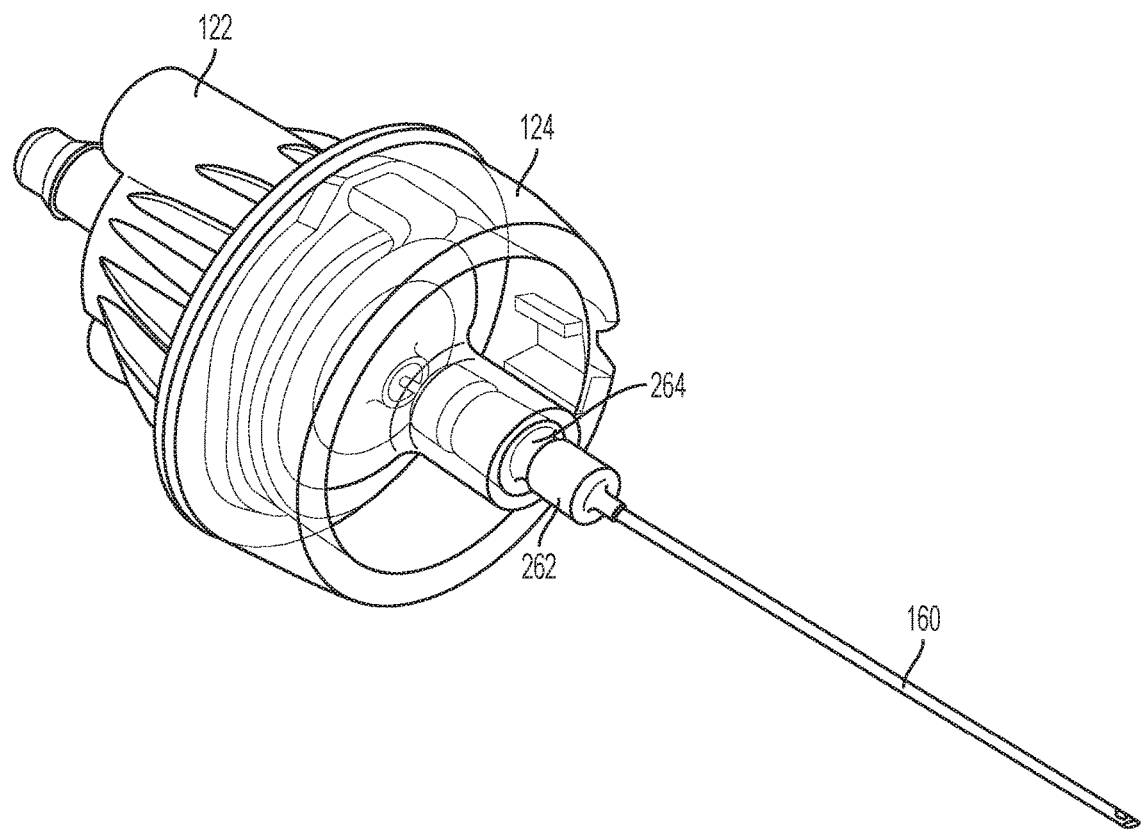
FIG. 6 is a perspective view, partially in phantom lines, of the example vitrectomy instrument of FIG. 3.
Figure 7:
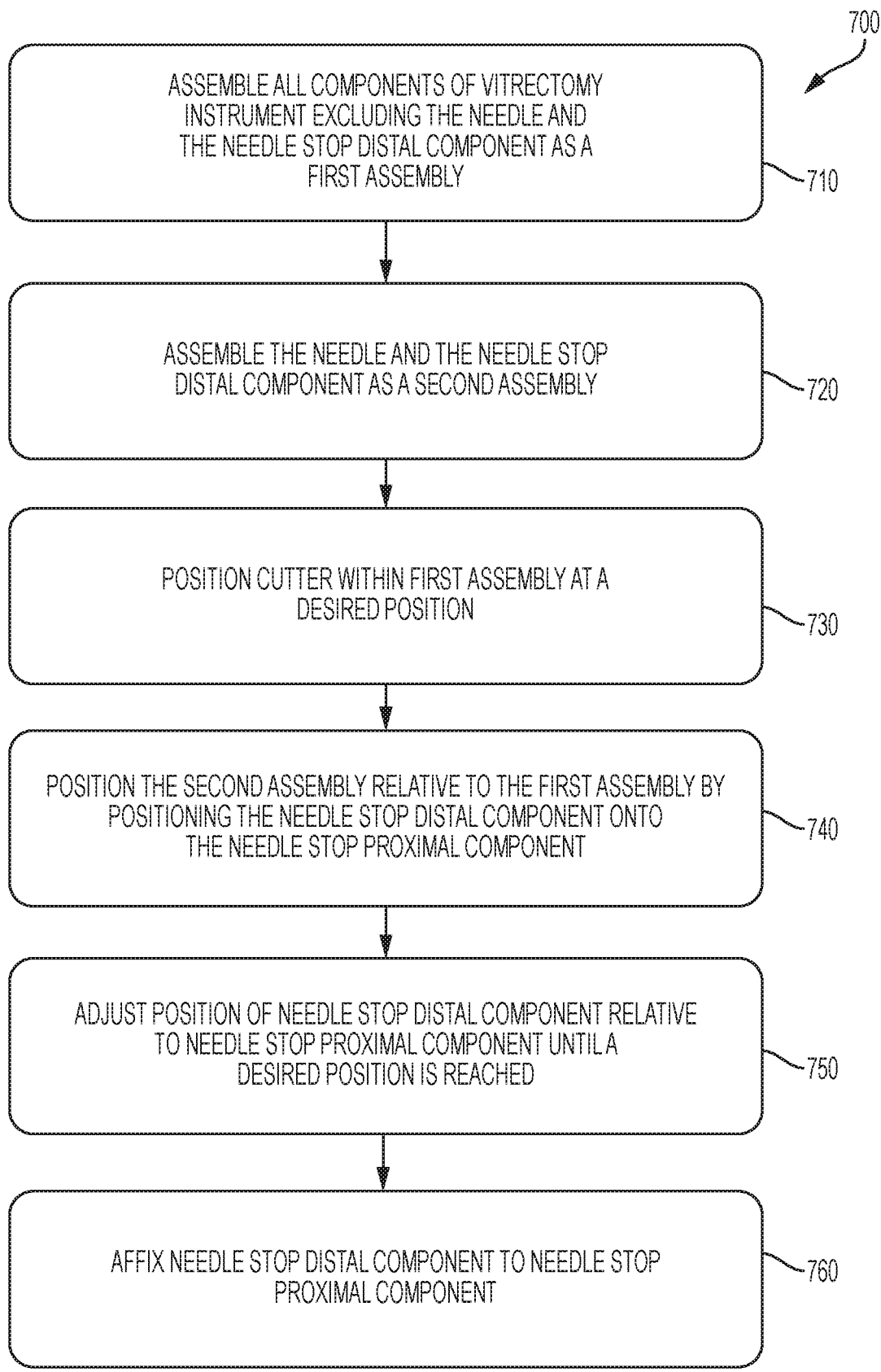
FIG. 7 is an example method of assembling a vitrectomy instrument.

FIG. 6 is a perspective view, partially in phantom lines, of the example vitrectomy instrument 100 of FIG. 3. FIG. 6 illustrates an example way in which the vitrectomy instrument 100 may be assembled, although other ways are within the scope of the disclosure. FIG. 7 is a flowchart 700 showing an example assembly procedure of a vitrectomy instrument within the scope of the disclosure, such as, for example, vitrectomy instrument 100. At 710, all of the components with the exception of the needle 160 and needle stop distal component 262 may be assembled together as a first assembly. At 720, the needle 160 and needle stop distal component 262 may be assembled together (e.g., by welding) as a second assembly. At 730, the inner tube 154 may be placed in a desired position, e.g., a known, fixed position for assembly purposes (e.g., the distal-most position), within the first assembly. At 740, the second assembly is positioned relative to the first assembly by positioning the needle stop distal component 262 over the needle stop proximal component 264, and, at 750, a position of the second assembly may be adjusted relative to the first assembly until a desired position is reached. At 760, the needle stop distal component 262 may be affixed (e.g., by welding) to the needle stop proximal component 264.

It will be appreciated by persons of skill in the art that the vitrectomy instrument 100 may be handled by an operator of the instrument, such as a physician performing an ophthalmic surgical operation, such as to remove vitreous fibers or to dissect/remove an epiretinal membrane. One or more connection lines may project from or be connected to a proximal end of the vitrectomy instrument 100, e.g., at ports 180 182, and 184. The connection lines may be used to connect the vitrectomy instrument 100 to a surgical console (not shown) suitable for use with implementations of the present disclosure. The connection lines may include one or more electrical connections, pneumatic tubes, aspiration tubes, irrigation tubes, and/or other lines. For example, one or more pneumatic connection lines may be coupled to ports 180 and 182 to provide for pneumatically driving the diaphragm 140 via the pneumatic passages 132, 134. One or more of the connection lines may include an aspiration tube for providing suction and/or for aspirating cut vitreous fibers from the vitrectomy instrument to the console. For example, an aspiration line may be coupled to port 184 to connect suction from the surgical console through the cutter tube 154 to the port 162. A reduced pressure or vacuum source in the console draws or aspirates the vitreous fibers from the eye through the port 162, the cutter tube 154, a channel of the vitrectomy instrument 100, the aspiration line, and into a collection device. The aspiration may be aided by a saline flushing solution or irrigant that is injected into the surgical site through an irrigation line.

The surgical console may be similar, for example, to that depicted in U.S. Pat. No. 8,579,929, the disclosure of which is incorporated herein by reference. The surgical console may be, for example, the CONSTELLATION® Vision System or the CENTURION® Vision System produced by Alcon Laboratories, Inc. of Fort Worth, Tex., or a system with similar capabilities in relation to a vitrectomy instrument as disclosed herein. The operation of the vitrectomy instrument 100 may be controlled by the operator using the console using one or more controls. The operation of the vitrectomy instrument 100 may be controlled by the operator using, for example, a foot pedal or other control device.

A vitrectomy instrument in accordance with implementations of the disclosure may be made of any desired material. For example, in some implementations, the needle 160, the needle stop 260, the needle stop distal component 262, the needle stop proximal component 264, the third cutter stop 250, the stop ring 254, and the cutter tube 154 may be formed from a metal, such as stainless steel or a titanium alloy. The dimensions may be any dimensions for use in a vitrectomy procedure. For example, the needle 160 may have an outer diameter sized for a 23 gauge, 25 gauge, or 27 gauge procedure.

Persons of ordinary skill in the art will recognize that, in addition to cutting and aspiration of vitreous fibers, instruments as described herein may also be used for other procedures, such as membrane cutting and aspiration, dissecting tissue, and lens removal.

Persons of ordinary skill in the art will appreciate that the implementations encompassed by the present disclosure are not limited to the particular exemplary implementations described above. In that regard, although illustrative implementations have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A vitrectomy instrument comprising:
a housing comprising:
a proximal end; and
a distal end;
a reciprocating cutter comprising:
a needle projecting from the distal end of the housing, the needle comprising:
a proximal end;
a distal end;
a first lumen; and
a port disposed at the distal end of the needle, the port providing fluid communication between an exterior of the needle and the first lumen;
an inner tube that extends within the first lumen of the needle, the inner tube comprising:
a second lumen; and
a cutting edge adapted to cut tissue drawn into the port; and
a needle stop coupled to the proximal end of the needle and comprising a first contact surface;
a cutter stop coupled to the inner tube and comprising a second contact surface, the first contact surface configured to contact the second contact surface limiting distal movement of the inner tube and defining a fully extended position of the inner tube; and
a motor operable to reciprocate the inner tube;
wherein the cutter stop further comprises a stop pad, and wherein the second contact surface is a surface of the stop pad.

2. The vitrectomy instrument of claim 1, wherein the motor comprises a diaphragm disposed in the housing and movable in response to pneumatic pressure, the diaphragm connected to the inner tube of the reciprocating cutter such that the inner tube is movable with the diaphragm.

3. The vitrectomy instrument of claim 2, wherein the diaphragm comprises a rigid diaphragm part connected to the inner tube and a flexible membrane connected to the rigid diaphragm part and to the housing.

4. The vitrectomy instrument of claim 1 wherein the cutter stop and the needle stop are formed from a metal.

5. The vitrectomy instrument of claim 1, wherein the cutter stop and the inner tube are formed from a metal and wherein the cutter stop is welded to the inner tube.

6. The vitrectomy instrument of claim 5, wherein the cutter stop comprises a stop ring that is welded to the inner tube.

7. The vitrectomy instrument of claim 1, wherein the cutter stop comprises a stop ring.

8. A vitrectomy instrument comprising:
a housing comprising:
a proximal end; and
a distal end;
a reciprocating cutter comprising:
a needle projecting from the distal end of the housing, the needle comprising:
a proximal end;
a distal end;
a first lumen; and
a port disposed at the distal end of the needle, the port providing fluid communication between an exterior of the needle and the first lumen:
an inner tube that extends within the first lumen of the needle, the inner tube comprising:
a second lumen; and
a cutting edge adapted to cut tissue drawn into the port; and
a needle stop coupled to the proximal end of the needle and comprising a first contact surface;
a cutter stop coupled to the inner tube and comprising a second contact surface, the first contact surface configured to contact the second contact surface limiting distal movement of the inner tube and defining a fully extended position of the inner tube; and
a motor operable to reciprocate the inner tube;
wherein the needle stop further comprises:
a needle stop proximal component;
a needle stop distal component coupled to the needle stop proximal component;
wherein the needle stop proximal component is received into a cavity defined by the needle stop distal component.

9. The vitrectomy instrument of claim 8, wherein the motor comprises a diaphragm disposed in the housing and movable in response to pneumatic pressure, the diaphragm connected to the inner tube of the reciprocating cutter such that the inner tube is movable with the diaphragm.

10. The vitrectomy instrument of claim 9, wherein the diaphragm comprises a rigid diaphragm part connected to the inner tube and a flexible membrane connected to the rigid diaphragm part and to the housing.

11. The vitrectomy instrument of claim 8 wherein the cutter stop and the needle stop are formed from a metal.

12. The vitrectomy instrument of claim 8, wherein the cutter stop and the inner tube are formed from a metal and wherein the cutter stop is welded to the inner tube.

13. The vitrectomy instrument of claim 12, wherein the cutter stop comprises a stop ring that is welded to the inner tube.

14. The vitrectomy instrument of claim 8, wherein the cutter stop comprises a stop ring.

15. A vitrectomy instrument comprising:
a housing comprising:
a proximal end; and
a distal end;
a reciprocating cutter comprising:
a needle projecting from the distal end of the housing, the needle comprising:
a proximal end;
a distal end;
a first lumen; and
a port disposed at the distal end of the needle, the port providing fluid communication between an exterior of the needle and the first lumen;
an inner tube that extends within the first lumen of the needle, the inner tube comprising:
a second lumen; and a cutting edge adapted to cut tissue drawn into the port; and a needle stop coupled to the proximal end of the needle and comprising a first contact surface;

a cutter stop coupled to the inner tube and comprising a second contact surface, the first contact surface configured to contact the second contact surface limiting distal movement of the inner tube and defining a fully extended position of the inner tube; and a motor operable to reciprocate the inner tube;

wherein the needle stop further comprises:

a needle stop proximal component;

a needle stop distal component coupled to the needle stop proximal component;

wherein the needle stop proximal component comprises:

a proximal portion having a first cross-sectional size;

a distal portion having a second cross-sectional size smaller than the first cross-sectional size; and a shoulder joining the proximal portion and the distal portion.

16. The vitrectomy instrument of claim 15, wherein the proximal portion of the needle stop proximal component is received into a cavity defined by the needle stop distal component.

17. The vitrectomy instrument of claim 16, wherein the needle stop proximal component is welded to the needle stop distal component.

18. The vitrectomy instrument of claim 15, wherein the shoulder defines the first contact surface.

19. The vitrectomy instrument of claim 15, wherein the motor comprises a diaphragm disposed in the housing and movable in response to pneumatic pressure, the diaphragm connected to the inner tube of the reciprocating cutter such that the inner tube is movable with the diaphragm.

20. The vitrectomy instrument of claim 19, wherein the diaphragm comprises a rigid diaphragm part connected to the inner tube and a flexible membrane connected to the rigid diaphragm part and to the housing.

21. The vitrectomy instrument of claim 15 wherein the cutter stop and the needle stop are formed from a metal.

22. The vitrectomy instrument of claim 15, wherein the cutter stop and the inner tube are formed from a metal and wherein the cutter stop is welded to the inner tube.

23. The vitrectomy instrument of claim 22, wherein the cutter stop comprises a stop ring that is welded to the inner tube.

24. The vitrectomy instrument of claim 15, wherein the cutter stop comprises a stop ring.

* * * * *